United States Patent [19]

Possis et al.

[11] Patent Number: 4,487,567

[45] Date of Patent: Dec. 11, 1984

[54] APPARATUS FOR MAKING A VASCULAR GRAFT

[75] Inventors: Zinon C. Possis; Demetre M. Nicoloff, both of Edina, Minn.

[73] Assignee: Possis Medical, Inc., Minneapolis, Minn.

[21] Appl. No.: 478,338

[22] Filed: Mar. 24, 1983

[51] Int. Cl.³ ............................................. B29C 27/00
[52] U.S. Cl. .................................... 425/403; 249/186
[58] Field of Search ................ 264/159; 249/184, 186; 425/403, 392, 470

[56] References Cited

U.S. PATENT DOCUMENTS

| | | | |
|---|---|---|---|
| 2,964,065 | 12/1960 | Haroldson et al. | 264/159 |
| 3,096,560 | 7/1963 | Liebig | 28/72 |
| 3,894,530 | 7/1975 | Dardik et al. | 128/1 |
| 3,929,957 | 12/1975 | Holden et al. | 264/159 |
| 3,974,526 | 8/1976 | Dardik et al. | 128/1 |
| 3,988,782 | 11/1976 | Dardik et al. | 3/1 |
| 4,167,388 | 9/1979 | Keelor et al. | 425/403 |
| 4,240,794 | 12/1980 | Holman et al. | 8/94.11 |
| 4,298,330 | 11/1981 | Davis | 425/403 |

*Primary Examiner*—Paul Lieberman
*Assistant Examiner*—W. Thompson
*Attorney, Agent, or Firm*—Burd, Bartz & Gutenkauf

[57] ABSTRACT

A mandrel assembly supports an umbilical cord during the shaping and curing of the cord for use as a vascular graft. The mandrel assembly has a pair of mandrel members adapted to be releasably connected in end-to-end relation. Adjacent end sections of the mandrel members have reduced cross sectional shapes to provide the graft with a Venturi throat. Each mandrel member has a low friction outer surface to facilitate the insertion and withdrawal of the mandrel member from the lumen of the umbilical cord.

17 Claims, 21 Drawing Figures

APPARATUS FOR MAKING A VASCULAR GRAFT

FIELD OF INVENTION

The invention relates to a support for shaping a tubular member. More particularly, the support is a mandrel for accommodating an umbilical cord during the forming and curing of the umbilical cord for use as a vascular graft.

BACKGROUND OF INVENTION

The use of human umbilical cords as vascular grafts in lieu of saphenous veins is disclosed in the prior art. The umbilical cords are processed for subsequent use in a living body. The umbilical cords are shaped and cured on a mandrel. Ho'man in U.S. Pat. No. 4,241,794 discloses a method of shaping a human umbilical cord to a configuration determined by a mandrel. The mandrel can have a J-shape or a U-shape. The umbilical cord is mounted on the mandrel and treated with alcohol to shrink the cord to the shape of the mandrel. An aldehyde solution is used to fix or cure the umbilical cords on the mandrel. The mandrel is then removed from the cured umbilical cord. The mandrel is a solid one-piece member of plastic, such as polyethylene. The plastic material of the mandrel is difficult to shape and machine to an accurate configuration. Accurate tolerances on plastic mandrels cannot be maintained. Metal mandrels are difficult to use to shape and cure umbilical cords, as these mandrels cannot be easily inserted into the lumen of an umbilical cord or withdrawn from a cured umbilical cord.

SUMMARY OF INVENTION

The invention broadly pertains to a mandrel assembly for supporting a tubular member to form and cure the tubular member to a vascular graft having a section for restricting the flow of fluid through the graft. The invention also includes a method of processing a human umbilical cord with a mandrel assembly for use as a vascular graft having a section for restricting the flow of fluid through the graft.

The mandrel assembly has a first mandrel member having a body and an end section located along a center line. The body and end section have an outer surface. The end section has a cross sectional area that is smaller than the cross sectional area of the body. A second mandrel member has a body and an end section located along the center line. The body and end section of the second mandrel member has an outer surface. The outer surfaces provide an elongated generally tubular shape used to determine the shape of the vascular graft. The end section of the second mandrel member has a cross sectional area smaller than the body attached thereto. This end section is shaped substantially the same as the cross sectional area and shape of the end section of the first mandrel member. Releasable means associated with the first and second mandrel members function to align the mandrel members, end sections, and outer surfaces, whereby the outer surfaces provide a support for an umbilical cord during the forming and curing thereof into a vascular graft having a section to restrict the flow of fluid through the graft. Each mandrel member has an outer low friction coating means to facilitate the insertion and withdrawal of the mandrel members from the umbilical cord. The coating means, such as polytetrafluoroethylene, provides the outer surfaces of the mandrel members with low friction characteristics. The coating means is secured to a metal core that defines the shape of the mandrel. The metal core has accurate tolerances and provides a rigid support for the coating means.

According to the preferred embodiment of the mandrel assembly used to form and cure a human umbilical cord into a vascular graft having a section for restricting the flow of fluid through the graft, there is provided first and second mandrel members, with outer continuous layers of low friction means to facilitate the insertion and removal of the mandrel members from the umbilical cord. The mandrel members have adjacent end sections that are smaller in cross sectional area than the main body of the mandrel members. Each end section has a truncated cone portion and a generally cylindrical portion terminated in an end. The ends have cooperating means that releasably connect the first and second mandrel members together to align the outer surfaces thereof so that the outer surfaces provide support for an umbilical cord during the formation and curing of the cord into a vascular graft having a section to restrict the flow of fluid through the graft. The cooperating means comprise a tapered hole in one of the ends of the mandrel member and a tapered projection on the other end of the other mandrel member. The projection is of a size and shape to fit into the hole to releasably lock the first and second mandrel members together.

The invention includes the method of processing an umbilical cord for use as a vascular graft having a section for restricting the fluid flow through the graft. The method uses a mandrel assembly comprising first and second mandrel members having cooperating means to releasably connect the mandrels together. The mandrel members also have means for making the section of the graft that restricts the flow of fluid through the graft. The method comprises the insertion of the first and second mandrel members into opposite ends of the uncured umbilical cord. The adjacent ends of the first and second mandrel members are connected together. The umbilical cord is then formed onto the outer surfaces of the mandrel members by shrinking the umbilical cord. This is accomplished with the use of ethyl alcohol. The shrunk umbilical cord is then cured or fixed on the mandrel members with an aqueous solution of dialdehyde. The cured umbilical cord is then removed from the first and second mandrel members and stored in a preservative solution for subsequent use.

IN THE DRAWINGS

DESCRIPTION OF PREFERRED EMBODIMENTS

Referring to FIGS. 1-7, there is shown a first embodiment of the mandrel assembly of the invention indicated generally at 20. Mandrel assembly 20 is used to support a human umbilical cord during the forming and curing of the cord to provide a cord with a blood flow restrictor section. The forming and curing process of the umbilical cord is hereinafter described. Mandrel assembly 20 can be used to make the entire or a portion of the vascular graft, disclosed in U.S. application Ser. No. 448,955, filed Dec. 13, 1982. The disclosure of this Application is included herein by reference.

Figure 7:
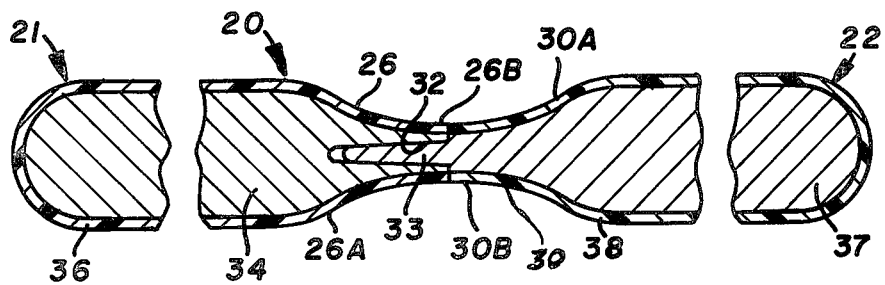
FIG. 7 is an enlarged foreshortened sectional view taken along the line 7—7 of FIG. 6.

Mandrel assembly 20 has a first elongated cylindrical member 21 releasably connected to a second elongated cylindrical member 22. First member 21 has an elongated linear cylindrical body 23 terminating in a semi-spherical outer end 24. The inner end of body 23 has a neck 26 terminating in a transverse annular inner end 27. As shown in FIG. 7, neck 26 has a truncated cone-shaped section 26A joined to a generally cylindrical section 26B. Section 26B has a diameter that is less than ½ the diameter of body 23. The diameter of the passage in section 26B can vary according to the throat size requirement of the vascular graft. For example, the diameter of the passage in section 26B can be 2 mm.

Figure 1:
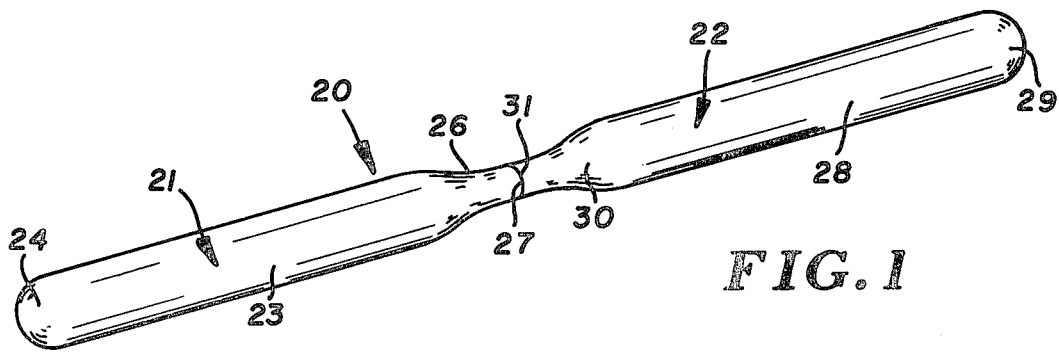
FIG. 1 is a perspective view of a mandrel assembly of the invention used to process and shape an umbilical cord for use as a vascular graft.
Figures 2, 3:
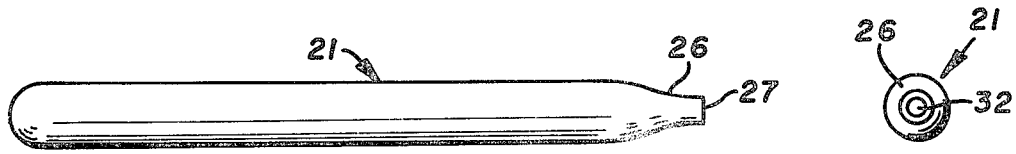
FIG. 2 is a side elevational view of a female mandrel section of the mandrel assembly of FIG. 1.
FIG. 3 is an end elevational view of the right end of FIG. 2.
Figure 5:
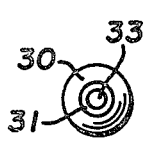
FIG. 5 is an end elevational view of the left end of FIG. 4.
Figure 4:
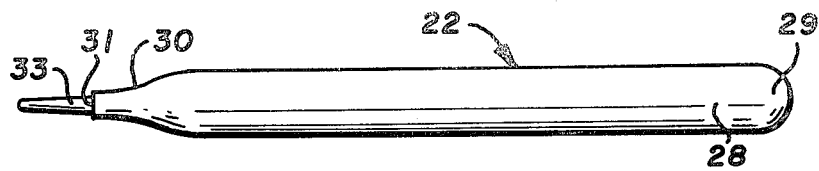
FIG. 4 is a side elevational view of a male mandrel section of the mandrel assembly of FIG. 1.
Figure 6:
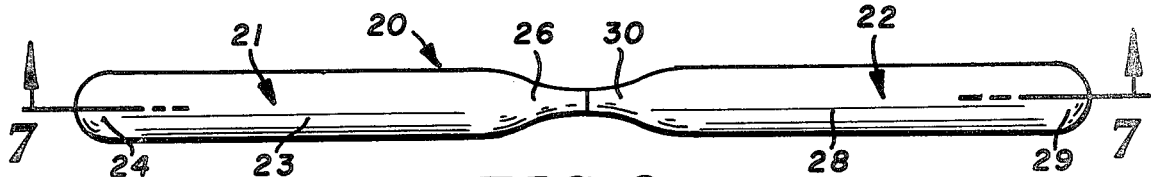
FIG. 6 is a side elevational view of the mandrel assembly.

The second member 22 has an elongated linear cylindrical body 28 having a semi-spherical shaped outer end 29. The inner end of body 28 has a neck 30 terminating in a transverse annular inner end 31. An axial finger or projection 33 extends along the longitudinal axis of member 22 away from end 31. Projection 33 has an outwardly converging taper of approximately 10 degrees relative to the longitudinal axis of body 28. The taper of projection 33 may be less than 10 degrees to facilitate inter-locking of the mandrel members 21 and 22 with each other. The outer end of projection 33 has a semi-spherical shape. As shown in FIG. 7, projection 33 fits into tapered hole 32 in neck 26 of mandrel member 21. Hole 32 is along the longitudinal axis of mandrel member 21 and tapers outwardly from the bottom end thereof. The taper of hole 32 is complementary to the taper of projection 33. Neck 30 has a truncated one section 30A joined to a generally cylindrical section 30B. The section 30B has a diameter that is less than ½ the diameter of the body 28. The diameter of section 30B is substantially the same as the diameter of section 26B. When mandrel members 21 and 22 are assembled together, as shown in FIGS. 1, 6, and 7, ends 27 and 31 are in engagement with each other and cylindrical surfaces 26B and 30B are coextensive with each other.

Referring to FIG. 7, first member 21 has a cylindrical rigid inner portion of core 34 of metal, such as stainless steel. Core 34 is preferably solid metal, which can be machines to an accurate configuration. The outer surface of core 34 is covered with a coating or outer layer 36 of low friction plastic material, such as polytetrafluoroethylene, known by the Trademark TEFLON. Other low friction plastic material can be used to coat cores 34 and 37. The second member 22 has a solid metal core 37 covered with an outer coating or layer 38 of low friction plastic material, such as TEFLON. The plastic material is applied to cores 34 and 37 with a conventional process. The plastic outer layers 36 and 38 are thin, continuous, uniform in thickness, and cover the entire outer surfaces of cores 34 and 37. The plastic material has a low coefficient of friction, which facilitates the insertion of the mandrel members 21 and 22 into the passage of a human umbilical cord. The plastic material is inert to umbilical cord tissue and the chemicals used to treat and cure the umbilical cord. The plastic outer layers 36 and 38 also facilitate the removal of the mandrel members 21 and 22 to form the formed and cured umbilical cord.

Figure 8:
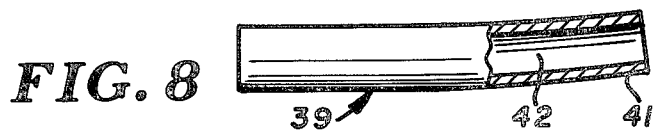
FIG. 8 is a side view, partly sectioned, of a human umbilical cord with the umbilical arteries and mesenchyme removed therefrom.

Referring to FIG. 8, there is shown a section of a human umbilical cord indicated generally at 39. The natural umbilical cord or funiculus umbilicalis has umbilical vessels embedded in loose mesenchyme or Wharton's jelly. The vessels comprise the umbilical vein and two umbilical arteries located around the vein. Cord 39 is a section of the umbilical vein comprising an elongated tubular wall 41 surrounding a continuous lumen or passage 42. The mesenchyme and umbilical arteries have been removed from the vein. Tubular wall 41 has a generally uniform diameter and must be formed and cured prior to its utilization as a vascular graft.

Figure 9:
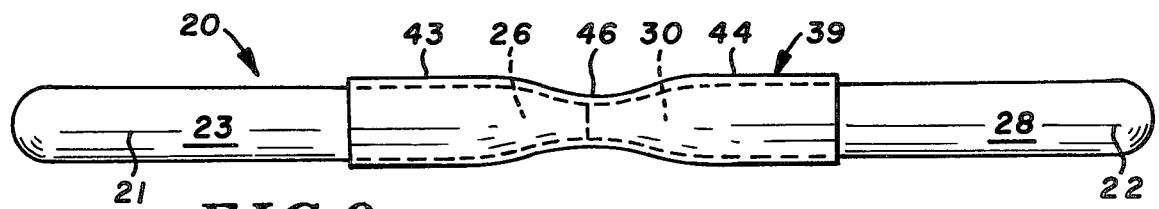
FIG. 9 is a longitudinal sectional view showing an umbilical cord mounted on the mandrel assembly.

Referring to FIG. 9, mandrel assembly 20 has been inserted into luman 42 of umbilical cord 39. Mandrel members 21 and 22 are inserted into opposite ends of umbilical cord 39 until their adjacent ends 27 and 31 contact each other. Projection 33 fits into tapered hole 32 to lock members 21 and 22 together. The umbilical cord 39 has opposite end portions 43 and 44 that are expanded by the cylindrical bodies 23 and 28. The mid-section of the cord section 39 is shrunk down and fits over neck sections 26 and 30 of mandrel assembly 20. An umbilical cord having umbilical arteries and mesenchyme can be placed on the mandrel assembly 20. The umbilical arteries and mesenchyme are removed from the umbilical vein during the processing procedure. The umbilical cord 39 is then treated, cured, and formed. A method of preparing the human umbilical cords for use in vascular replacement is disclosed by Holman et al. in U.S. Pat. No. 4,240,794. The human umbilical cord is initially flushed to removed loose tissue and other substances therefrom. The cord is mounted on mandrel assembly 20, as hereinafter described. The mandrel assembly 20 supporting the umbilical cord, as shown in FIG. 9, is immersed in ethyl alcohol for a period of time of at least 18 hours. The immersion in ethyl alcohol is maintained until the umbilical cord 39 is substantially dehydrated. The umbilical cord 39, during the dehydration, shrinks onto mandrel assembly 20. This forms the umbilical cord. A portion of the umbilical cord is shrunk down and fits over the neck sections 26 and 30 of mandrel assembly 20, thereby forming a Venturi throat section 46 in the umbilical cord 39. The dehydrated umbilical cord 39 mounted on mandrel assembly 20 is then immersed into an aqueous solution of dialdehyde starch to cure or fix the umbilical cord 39. The umbilical cord 39 is treated with the aqueous solution for a period of time for about 18 hours. The cord 39 is then stored for subsequent use as a vascular graft. A mesh sleeve (not shown) can be placed over cord 39 to provide additional reinforcement for the wall of the cord. Mandrel assembly 20 can be used with other processes for removing the umbilical arteries, mesenchyme, and forming and fixing human umbilical cords for use as vascular grafts.

In use, umbilical cord 39 is located on mandrel assembly 20, as shown in FIG. 9. The neck end 26 of mandrel member 21 is inserted into one end of lumen 42. The neck end 30 of the second mandrel member 22 is inserted into the opposite end of lumen 42. The mandrel members 21 and 22 are longitudinally moved together into a locking relationship. The low friction plastic layers 36 and 38 of mandrel members 21 and 22 facilitate the slipping of the mandrel members 21 and 22 into the lumen of the umbilical cord. Projection 33 fits into tapered hole 32. The complementary tapers of hole 32 and projection 33 provide a self-locking action that holds mandrel sections 21 and 22 together. Umbilical cord 39 has expanded end portions 43 and 44 located about mandrel members 23 and 28. The center portion of umbilical cord 39 has a reduced cross sectional area throat section 46 located about engaging necks 26 and 30. The umbilical cord 39 on mandrel assembly 20, as shown in FIG. 9, is cured. During the curing process, the tubular wall 41 of umbilical cord 39 is shaped in a manner determined by the shape of mandrel assembly 20.

Figure 10:
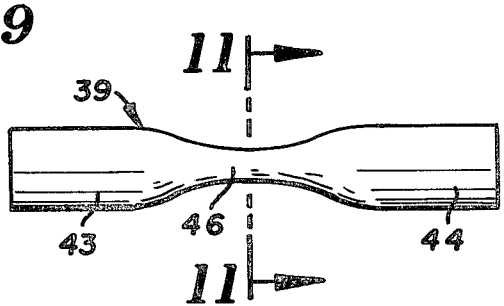
FIG. 10 is a side elevational view of the section of the umbilical cord having a reduced diameter throat to restrict blood flow through the cord made with the use of the mandrel assembly.
Figure 11:
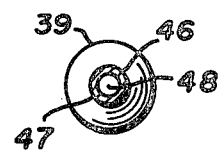
FIG. 11 is a sectional view taken along the line 11—11 of FIG. 10.
Figure 12:
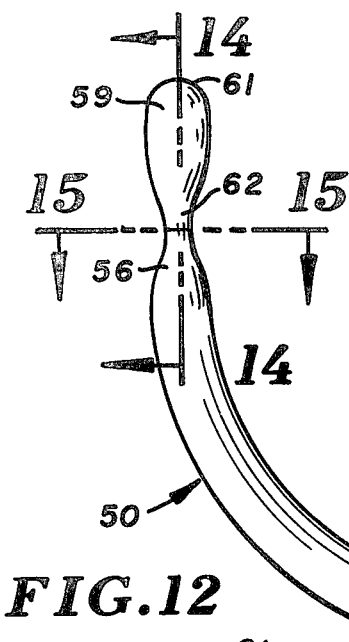
FIG. 12 is a side elevational view of a modified mandrel assembly of the invention used to process and shape an umbilical cord for use as a vascular graft.

The shape of the curved umbilical cord 39 is shown in FIG. 10. The throat section 46 of umbilical cord 39 has a generally cylindrical wall 47 surrounding a passage 48. The passage 48 is in longitudinal communication with the passages in the opposite ends of the umbilical cord 39 so as to allow continuous blood flow through the cured umbilical cord 39. Passage 48 is a throat having a cross sectional area that is substantially less than the cross sectional area of the passages in the end sections 43 and 44. Preferably, the cross sectional area of passage 48 is less than ¼ of the cross sectional area of the lumen of sections 43 and 44. The cross sectional areas of sections 43 and 44 are substantially the same. For example, the cross sectional area of the body passage can be 19.6 mm$^2$ and the cross sectional area of the passage of throat section 48 can be 3.14 mm$^2$. Other cross sectional area sizes of the lumen can be made on mandrel assembly 20.

Figure 13:
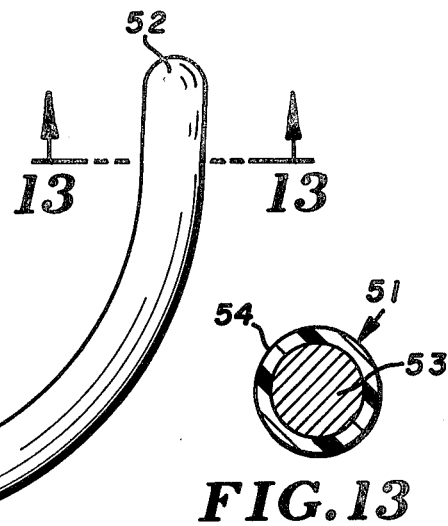
FIG. 13 is an enlarged sectional view taken along the line 13—13 of FIG. 12.
Figure 14:
FIG. 14 is an enlarged foreshortened sectional view taken along the line 14—14 of FIG. 12.
Figure 15:
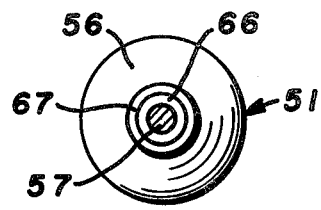
FIG. 15 is an enlarged sectional view taken along the line 15—15 of FIG. 12.

Referring to FIGS. 12-15, there is shown a second embodiment of the mandrel assembly of the invention indicated generally at 50 for accommodating a human umbilical cord during forming and curing thereof. Mandrel assembly 50 has a first generally U-shaped mandrel member 51 releasably connected to a second mandrel member 59. Mandrel member 51 has a semi-spherical proximal end 52 and a neck or distal end 56. Mandrel member 51 has a U-shaped curved metal core 53. The entire outer surface of core 53 is shown in FIGS. 13 and 14 as coated with a layer of low friction plastic material 54, such as polytetrafluoroethylene, known as TEFLON, to facilitate the insertion and removal of the mandrel members 51 and 59 into and from the umbilical cord 68. As shown in FIG. 14, neck end 56 has a projection 57 extended outwardly along the longitudinal axis or center line of neck end 56. Projection 57 is generally cone-shaped and has an outwardly directed converging taper. The diameter of the base of projection 57 is smaller than the diameter of the end of the neck end 56. An annular generally flat end wall 58 surrounds the base of projection 57. Coating layer 56 extends to end wall 58. Neck end 56 has a generally truncated cone section 56A that is joined to a cylindrical section 56B.

The second mandrel member 59 has a semi-spherical outer end 61 and a neck end 62 opposite the end 61. Neck end 62 has a truncated cone section 62A joined to a cylindrical section 62B. The section 62B terminates in a flat end 63 having a tapered longitudinal hole 64. Hole 64 and projection 57 have a complementary converging taper. Preferably, the taper is 10 degrees or less so that the projection locks into hole 64 when second mandrel member 59 is placed in assembled relation with the first mandrel member 51. Mandrel member 59 has a metal core 66. The outer surface of core 66 is covered with a coating layer 67, such as a low friction plastic material, as polytetrafluoroethylene.

Figure 16:
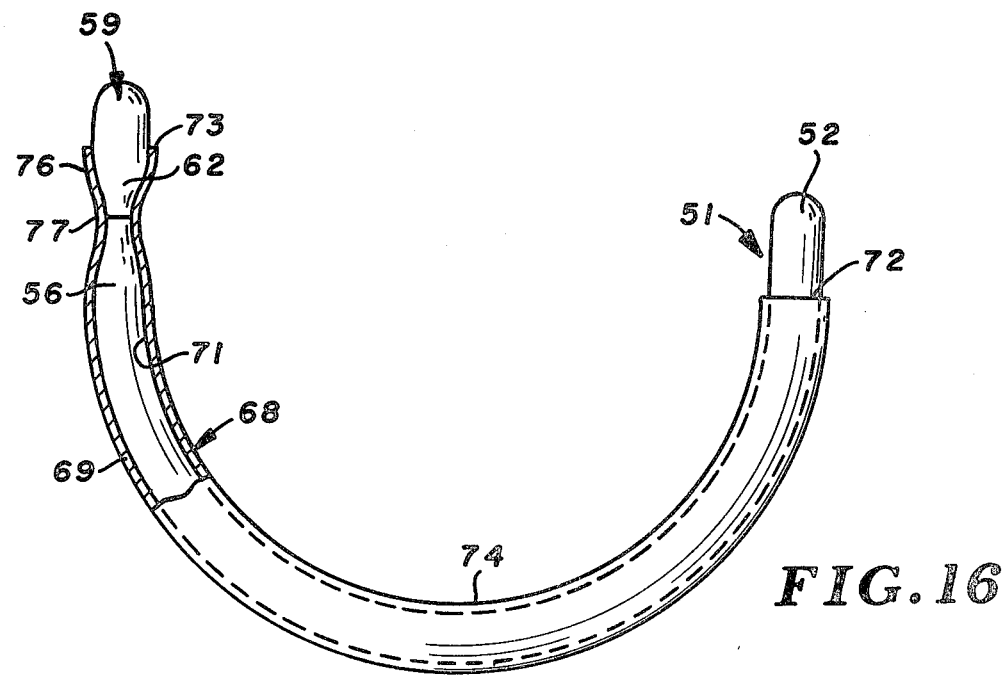
FIG. 16 is a side elevational view, partly sectioned, of the mandrel assembly of FIG. 12 supporting a human umbilical cord.
Figure 17:
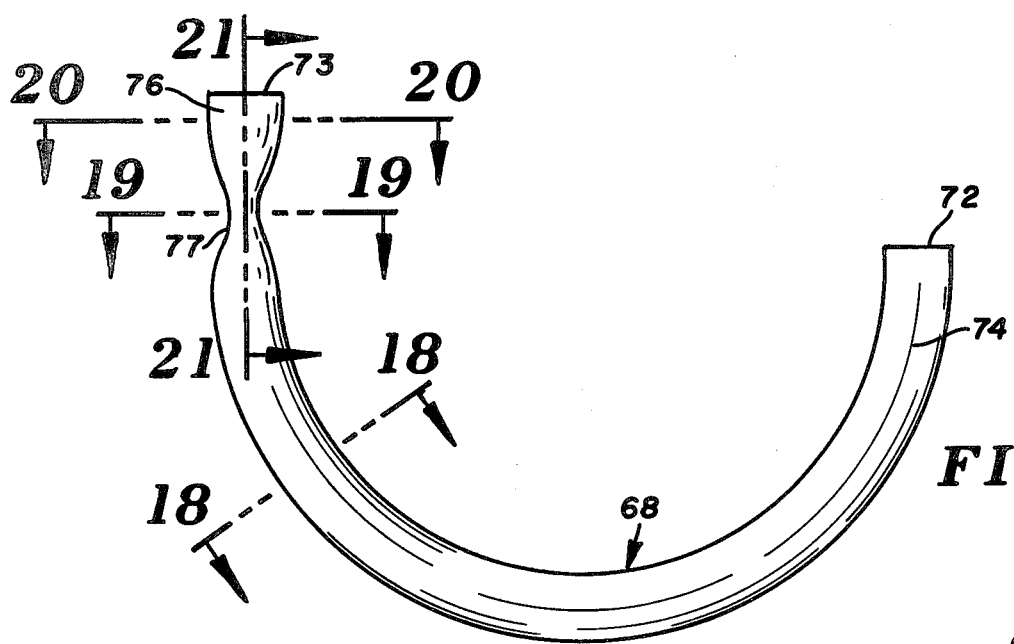
FIG. 17 is a side elevational view of the umbilical cord formed and cured on the mandrel assembly of FIG. 12 with the mandrel assembly removed from the cord.
Figure 18:
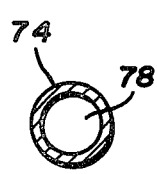
FIG. 18 is an enlarged sectional view taken along the line 18—18 of FIG. 17.
Figure 19:
FIG. 19 is an enlarged sectional view taken along the line 19—19 of FIG. 17.
Figure 20:
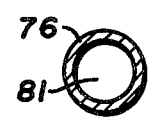
FIG. 20 is an enlarged sectional view taken along the line 20—20 of FIG. 17.
Figure 21:
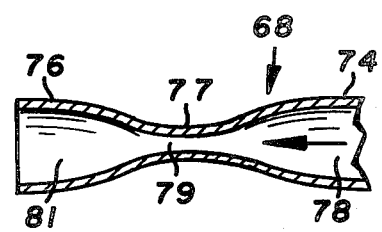
FIG. 21 is an enlarged sectional view taken along the line 21—21 of FIG. 17.

Referring to FIG. 16, there is shown mandrel assembly 50 in assembled relation with an umbilical cord 68 to provide a support for the process to form and cure the umbilical cord 68. First mandrel member 51 is inserted through end 72 of umbilical cord 68. The inside diameter of the umbilical cord is slightly expanded. The neck end 56 is located inwardly of the umbilical cord end 73. The second mandrel member 59 is inserted into end 73. After the umbilical cord 68 is cured, the mandrel members 51 and 59 are withdrawn from the opposite ends of the cured umbilical cord. The low friction coating layers 54 and 67 have continuous outer surfaces that facilitate the insertion of the mandrel members 51 and 59 into the opposite ends of the umbilical cord and the extraction of the mandrel members 51 and 59 from the cured and formed umbilical cord.

As shown in FIGS. 17-21, the cured umbilical cord 68 has a body or proximal section 74 extended from the proximal end 72 to throat section 77. Throat section 77 is joined to distal section 76. Distal section 76 terminates at distal end 73. Proximal section 71 has a passage 78 leading to a throat passage 79 surrounded by throat section 77. Passage 79 is open to a distal passage 81. The cross sectional area of throat section 79 is substantially smaller than the cross sectional area of the proximal passage 78. The cross sectional area of proximal passage 81 is substantially the same as the cross sectional area of the proximal passage 78. The umbilical cord having the throat section 77 is used as a vascular graft in the manner disclosed in U.S. patent application Ser. No. 448,955, filed Dec. 13, 1982. The disclosure of this Application is incorporated herein by reference.

While there has been shown and described two embodiments of the mandrel assembly of the invention, it is understood that changes in the size, shape, length of the mandrel members may be made by those skilled in the art without departing from the invention. The invention is defined in the following claims.

The embodiments of the invention in which an exclusive property or privilege is claimed are defined as follows:

1. A mandrel assembly for use in forming and curing tubular member into a vascular graft having a section for restricting fluid flow through the graft comprising: a first mandrel member having a body and an end section located along a center line, said body and an end section having an outer surface, said end section and outer surface thereon having a cross sectional area smaller than the cross sectional area of the body, and outer surface thereon, a second mandrel member having a body and an end section located along a center line, said body and end section of the second mandrel member having an outer surface, said end section and outer surface thereon for the second mandrel member having a cross sectional area and shape substantially the same as the cross sectional area and shape of the end section and outer surface thereon of the first mandrel member, and means releasably connecting the first and second mandrel members in end-to-end relation and aligning the center lines, end sections, and outer surfaces of the mandrel members, said outer surfaces providing support for a tubular member during the forming and curing thereof into a vascular graft having a section to restrict the flow of fluid through the graft.

2. The mandrel assembly of claim 1 wherein: each mandrel member has an outer low friction coating means, said coating means having said outer surface.

3. The mandrel assembly of claim 2 wherein: the coating means is a low friction plastic material.

4. The mandrel assembly of claim 1 wherein: each end section has a truncated cone portion and a generally cylindrical portion terminating in an end, said outer surface of each end section surrounding the cone portion and cylindrical portion.

5. The mandrel assembly of claim 4 wherein: each mandrel member has an outer low friction coating means, said coating means having said outer surface.

6. The mandrel assembly of claim 1 wherein: the first mandrel member is a first linear cylindrical member, and the second mandrel member is a second linear cylindrical member.

7. The mandrel assembly of claim 1 wherein: the first mandrel member is a curved elongated member.

8. A mandrel assembly for use in forming and curing an umbilical cord into a vascular graft having a section for restricting fluid flow through the graft comprising: a first mandrel member having a body and an end section located along a center line, said body and end section having an outer surface, said end section having a cross sectional area smaller than the cross sectional area of the body, a second mandrel member having a body and an end section located along the center line, said body and end section of the second mandrel member having an outer surface, said end section of the second mandrel member having a cross sectional area and shape substantially the same as the cross sectional area and shape of the end section of the first mandrel member, and means releasably connecting the first and second mandrel members in end-to-end relation and aligning the center lines, end sections, and outer surfaces of the first and second mandrel members, said means releasably connecting the first and second mandrel members includes an outwardly diverging hole in one member and an outwardly converging projection of a size to fit into the hole, said hole and projection being located along the center lines of said members said hole and projection having engaging surfaces tapered at an angle of 10° or less relative to the aligned center lines of the members to releasably hold the first and second mandrel members in assembled relation with each other, said outer surfaces providing support for an umbilical cord during the forming and curing thereof into a vascular graft having a section to restrict the flow of fluid through the graft.

9. The mandrel assembly of claim 8 wherein: each mandrel member has an outer low friction coating means, said coating means having said outer surface.

10. The mandrel assembly of claim 8 wherein: each end section has a truncated cone portion and a generally cylindrical portion terminating in an end, the outer surface of each end section surrounding the cone portion and cylindrical portion.

11. A mandrel assembly for use in forming and curing an umbilical cord into a vascular graft having a section for restricting the flow of fluid through the graft comprising: a first member having a core and a first layer of low friction means covering the core, said first layer having a continuous outer surface, said member having a first end, a second end opposite the first end having an outer surface smaller in cross sectional area than the cross sectional area of the first end, and outer surface thereon and a center line extended between said ends, a second member having a core and a second layer of low friction means covering the core of the second member, said second layer having a continuous outer surface, said second member having a first end, a second end opposite the first end having an outer surface smaller in cross sectional area than the cross sectional area of the first end and outer surface thereon of the second member, and a center line between the ends thereof, said second ends of the first and second members having cooperating means releasably connecting the first and second members together to align the outer surfaces of said second ends thereof whereby said outer surfaces provide support for an umbilical cord during the forming and curing thereof into a vascular graft having a section to restrict the flow of fluid through the graft.

12. The mandrel assembly of claim 11 wherein: the first member is a first linear cylindrical member, and the second member is a second linear cylindrical member.

13. A mandrel assembly for use in forming and curing an umbilical cord into a vascular graft having a section for restricting the flow of fluid through the graft comprising: a first member having a core and a first layer of low friction means covering the core, said first layer having a continuous outer surface, said member having a first end, a second end opposite the first end smaller in cross sectional area than the cross sectional area of the first end, and a center line extended between said ends, said first member being a curved elongated member, a second member having a core and a second layer of low friction means covering the core of the second member, said second layer having a continuous outer surface, said second member having a first end, a second end opposite the first end smaller in cross sectional area than the cross sectional area of the first end of the second member, and a center line between the ends thereof, said second ends of the first and second members having corporating means releasably connecting the first and second members together to align the outer surfaces of said first ends thereof whereby said outer surfaces provides support for an umbilical cord during the forming and curing thereof into a vascular graft having a section to restrict the flow of fluid through the graft.

14. The mandrel assembly of claim 13 wherein: the second member is a linear cylindrical member.

15. A mandrel assembly for use in forming and curing an umbilical cord into a vascular graft having a section for restricting the flow of fluid through the graft comprising: a first member having a core and a first layer of low friction means covering the core, said first layer having a continuous outer surface, said member having a first end, a second end opposite the first end smaller in cross sectional area than the cross sectional area of the first end, and a center line extended between said ends, second member having a core and a second layer of low friction means covering the core of the second member, said second layer having a continuous outer surface, said second member having a first end, a second end opposite the first end smaller than cross sectional area than the cross sectional area of the first end of the second member, and a center line between the ends thereof, said second ends of the first and second members having corporating means releasably connecting the first and second members together to align the surfaces of said second ends thereof whereby said outer surfaces provide support for an umbilical cord during the forming and curing thereof into a vascular graft having a section to restrict the flow of fluid through the graft, said cooperating means comprise a tapered hole in one of said second ends and a tapered projection on the other of said second ends, said hole and projection having engaging surfaces tapered at an angle of 10° or less relative to the aligned center line of the members to releasably lock the first and second mandrel members.

16. The mandrel assembly of claim 15 wherein: each second end has a truncated cone section and a generally cylindrical section terminating in an end.

17. The mandrel assembly of claim 11 wherein: each second end has a truncated cone section and a generally cylindrical section, said cylindrical section being smaller in cross section than the cross section of the core.

* * * * *